(12) United States Patent
Jaworski et al.

(10) Patent No.: US 8,394,329 B2
(45) Date of Patent: Mar. 12, 2013

(54) OPTICAL DEVICE FOR DETECTION OF AGENT

(75) Inventors: Frank B. Jaworski, Goleta, CA (US); Anuradha M. Agarwal, Weston, MA (US)

(73) Assignees: Raytheon Company, Waltham, MA (US); Massachusetts Institute of Technology, Cambridge, MA (US)

( * ) Notice: Subject to any disclaimer, the term of this patent is extended or adjusted under 35 U.S.C. 154(b) by 849 days.

(21) Appl. No.: 12/503,264

(22) Filed: Jul. 15, 2009

(65) Prior Publication Data

US 2012/0154810 A1 Jun. 21, 2012

Related U.S. Application Data

(60) Provisional application No. 61/223,546, filed on Jul. 7, 2009.

(51) Int. Cl.
*G01N 21/00* (2006.01)
*G02B 6/00* (2006.01)
*G02B 6/42* (2006.01)
*G01J 1/04* (2006.01)

(52) U.S. Cl. ............ 422/82.11; 422/82.06; 422/82.07; 422/82.08; 422/82.09; 356/432; 356/433; 250/227.14; 250/227.19; 385/12; 385/15; 385/30; 385/39; 385/50

(58) Field of Classification Search ............ None
See application file for complete search history.

(56) References Cited

U.S. PATENT DOCUMENTS

| | | | |
|---|---|---|---|
| 7,389,025 B2 * | 6/2008 | Smith et al. ............ 385/39 |
| 2005/0035278 A1 * | 2/2005 | Margalit et al. ......... 250/227.14 |
| 2005/0110992 A1 * | 5/2005 | Scherer et al. ............ 356/318 |
| 2007/0211985 A1 * | 9/2007 | Duer .................... 385/12 |
| 2008/0265147 A1 * | 10/2008 | Fan et al. ............ 250/227.24 |

OTHER PUBLICATIONS

Hu et al.; "Si—CMOS—compatible lift-off fabrication of low-loss planar chalcogenide waveguides"; Optics Express, vol. 15, No. 19; pp. 10, Sep. 17, 2007.
Hu et al.; "Demonstration of chalcogenide glass racetrack microresonators"; Optics Letters, vol. 33, No. 8; pp. 761-763, Apr. 15, 2008.
U.S. Appl. No. 12/948,453, filed Nov. 17, 2010, Jaworski, et al., *Optical Device for Detection of an Agent*. (CIP of 0117).
U.S. Appl. No. 12/948,485, filed Nov. 17, 2010, Jaworski, et al., *Optical Device for Detection of an Agent*. (CIP of 0117).
U.S. Appl. No. 13/173,221, filed Jun. 30, 2011, Frank B. Jaworski, *Optical Device for Detection of an Agent*.

* cited by examiner

*Primary Examiner* — Neil N Turk
(74) *Attorney, Agent, or Firm* — Lando & Anastasi, LLP

(57) ABSTRACT

An agent sensing system may comprise an emitter optical resonator, a functionalized optical resonator, and a reference optical resonator. The emitter optical resonator may be configured to emit light at one or more system peak wavelengths. The functionalized optical resonator may be optically coupled to the emitter optical resonator and configured to propagate the emitted light in the absence of a particular agent, and filter the emitted light in the presence of the particular agent. The reference optical resonator may be optically coupled to at least one of the emitter optical resonator and the functionalized optical resonator such that an intensity of light propagated by the reference optical resonator is based at least on whether light emitted by the emitter optical resonator is filtered or propagated by the functionalized optical resonator.

18 Claims, 3 Drawing Sheets

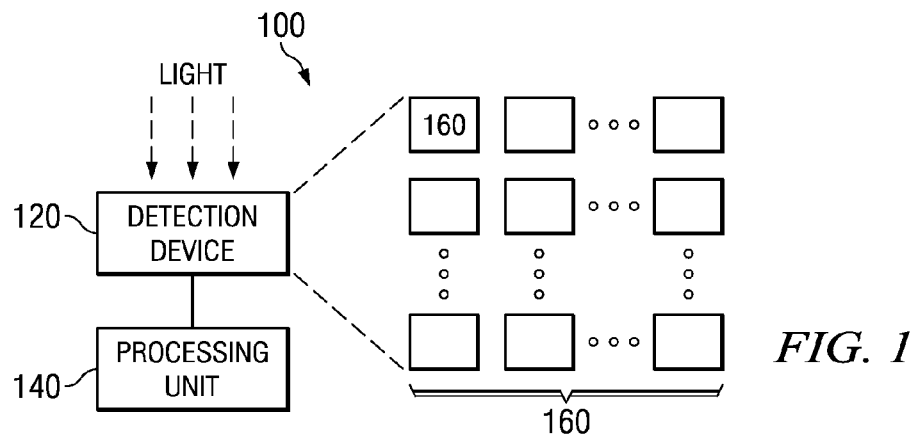
FIG. 1
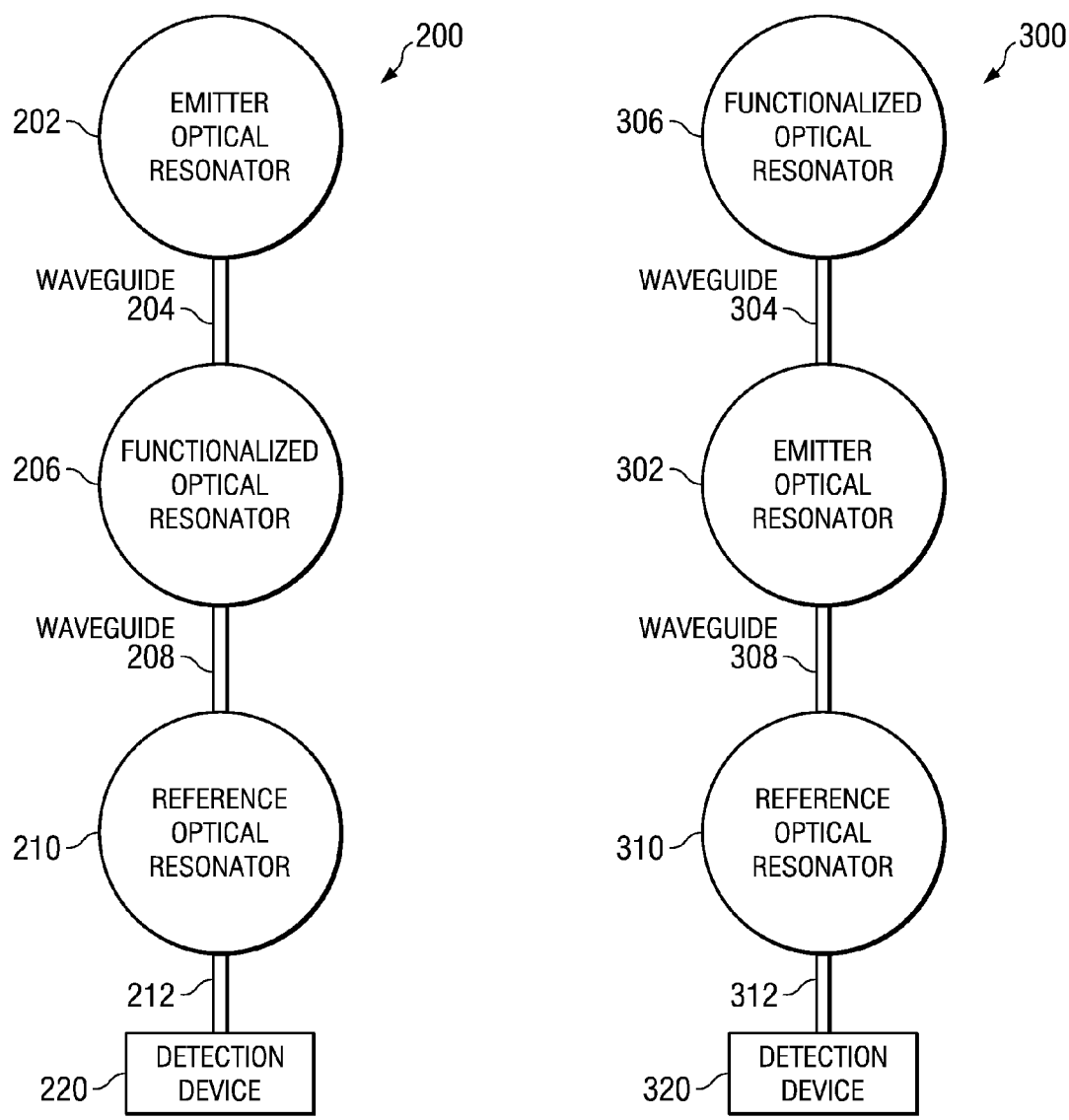
FIG. 2
FIG. 3

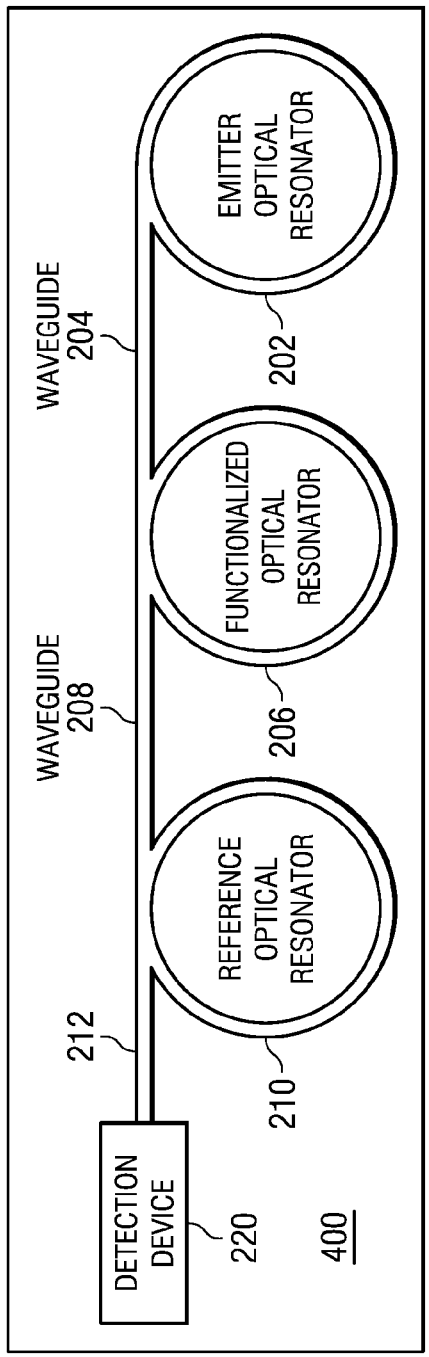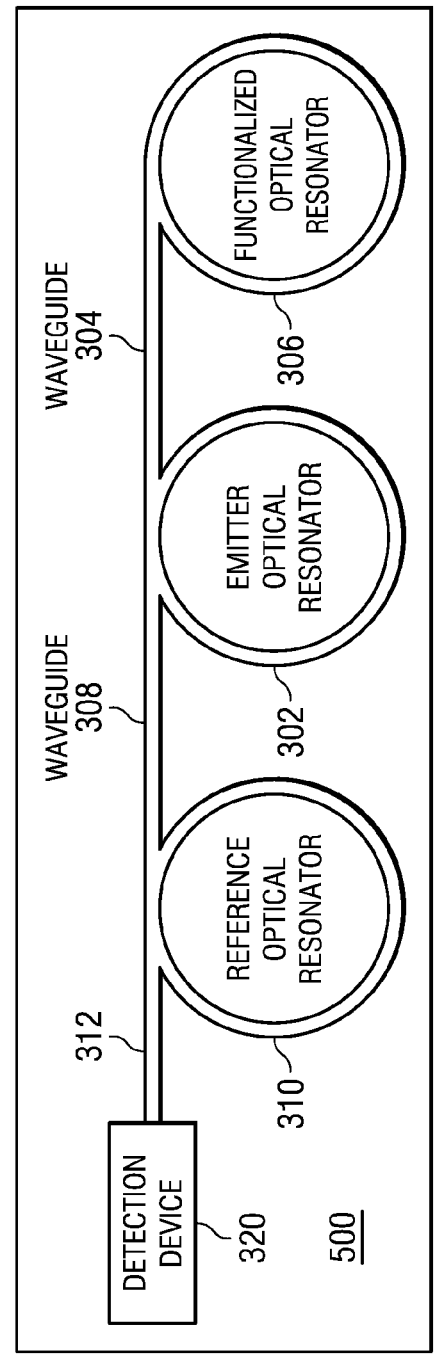

OPTICAL DEVICE FOR DETECTION OF AGENT

RELATED APPLICATION

This application claims the benefit of U.S. Provisional patent application Ser. No. 61/223,546 filed Jul. 7, 2009, the contents of which is incorporated by reference in its entirety.

TECHNICAL FIELD

This disclosure relates in general to optical sensing and more particularly to an optical sensing system and method for sensing the presence of an agent.

BACKGROUND

Photodetector circuits are utilized in various devices (e.g., focal plane arrays and other photo-sensing circuits) to sense incident light in the visible and non-visible spectra. Many attempts have been made to employ photodetectors to detect the presence of certain agents (e.g., the presence of biological, chemical, and/or hazardous agents). However, the present of certain agents proximate to a photodetector may not significantly affect the intensity of light incident on the photodetector, but instead the peak wavelength(s) of the incident light may shifted. Accordingly, photodetectors suited to detect light intensity are often not practical for use of detecting the presence of agents.

SUMMARY OF THE DISCLOSURE

According to one embodiment, an agent sensing system may comprise an emitter optical resonator, a functionalized optical resonator, and a reference optical resonator. The emitter optical resonator may be configured to emit light at a system peak wavelength or a plurality of system peak wavelengths. The functionalized optical resonator may be optically coupled to the emitter optical resonator and configured to propagate the emitted light in the absence of a particular agent, and filter the emitted light in the presence of the particular agent. The reference optical resonator may be optically coupled to at least one of the emitter optical resonator and the functionalized optical resonator such that an intensity of light propagated by the reference optical resonator is based at least on whether light emitted by the emitter optical resonator is filtered or propagated by the functionalized optical resonator.

Technical advantages of certain embodiments may include an agent sensing device that may be integrated with or form part of an optical sensing device, thus potentially reducing size, weight, cost, and power requirements as compared to traditional agent sensing devices.

Other technical advantages will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present disclosure and its advantages, reference is now made to the following description, taken in conjunction with the accompanying drawings, in which:

FIG. 1 depicts a simplified schematic diagram illustrating an example optical sensing system, in accordance with embodiments of the present disclosure;

FIG. 2 depicts a simplified schematic diagram illustrating an example agent sensing system, in accordance with embodiments of the present disclosure;

FIG. 3 depicts a simplified schematic diagram illustrating another example agent sensing system, in accordance with embodiments of the present disclosure;

FIG. 4 depicts a plan view of an example substrate with selected components of the agent sensing system depicted in FIG. 2 formed thereon, in accordance with embodiments of the present disclosure;

FIG. 5 depicts a plan view of an example substrate with selected components of the agent sensing system depicted in FIG. 3 formed thereon, in accordance with embodiments of the present disclosure.

DETAILED DESCRIPTION OF THE DISCLOSURE

Figure 6A:
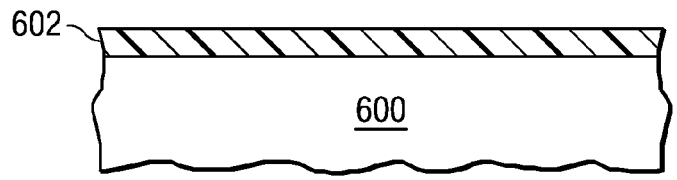
FIGS. 6A-6F depict a cross-sectional view of a substrate during various stages of fabrication of selected components of an agent sensing system, in accordance with embodiments of the present disclosure.

Embodiments of the present disclosure and its advantages are best understood by referring to FIGS. 1 through 6F of the drawings, like numerals being used for like and corresponding parts of the various drawings.

FIG. 1 is a block diagram illustrating optical sensing system 100, in accordance with embodiments of the present disclosure. For example, imaging system 100 may be a digital camera, video camera, or any other photographic and/or image capturing device. Imaging system 100 may include detection device 120 and processing unit 140. Detection device 120 may be a focal plane array (FPA), active pixel sensor (APS) or any other suitable light sensing device that can capture images. Detection device 120 may include, for example, one or more diodes, charge-coupled devices (CCDs), or any other suitable photovoltaic detectors or transducers. Processing unit 140 may be a combination of hardware, software, or firmware that is operable to receive signal information from detection device 120 and convert the signal information into an electronic image.

Detection device 120 may include an array of unit cells 160. Unit cells 160 may accumulate charge or produce a current and/or voltage in response to light incident upon the unit cell and may correspond to a pixel in a captured electronic image. The accumulated charge or the produced current and/or voltage may be used by processing unit 140 for processing of the incident light (e.g., to create an image representative of the incident light). In certain embodiments, one or more of unit cells 160 may include a position sensitive detector (PSD), photodiode, and/or any other suitable device for accumulating a charge and/or producing a current and/or voltage in response to light incident upon the unit cell.

FIG. 2 depicts a simplified schematic diagram illustrating an example agent sensing system 200, in accordance with embodiments of the present disclosure. As depicted in FIG. 2, agent sensing system 200 may include emitter optical resonator 202, functionalized optical resonator 206, reference optical resonator 210, waveguides 204, 208, and 212, and detection device 220.

Each of emitter optical resonator 202, functionalized optical resonator 206, and reference optical resonator 210, may include any device, system, or apparatus configured to form a standing wave of one or more wavelengths of visible and/or non-visible light. In certain embodiments, emitter optical resonator 202, functionalized optical resonator 206, and reference optical resonator 210 may each be configured to form a standing wave of the same peak wavelength(s).

In some embodiments, one or more of emitter optical resonator 202, functionalized optical resonator 206, and reference optical resonator 210 may comprise a waveguide configured in a closed loop known as an optical ring such that when light of the appropriate wavelength(s) is/are coupled to the loop, the light increases in intensity over multiple round-trips due to constructive interference. Other wavelengths of light may decrease in intensity due to destructive interference. Such optical rings may be made of materials, and may have sizes and configurations suitable to form standing waves of desired wavelength(s).

In other embodiments, one or more of emitter optical resonator 202, functionalized optical resonator 206, and reference optical resonator 210 may comprise an arrangement of mirrors known as an optical cavity and configured to form a standing wave for one or more wavelengths. Such optical cavities may be made of materials, and may have sizes and configurations suitable to form standing waves of desired wavelengths.

In agent sensing system 200, emitter optical resonator 202 may operate as a light source. Accordingly, emitter optical resonator 202 may include or be optically coupled to one more components configured to produce light at the peak wavelength(s) of emitter optical resonator 202. For example, emitter optical resonator 202 may include quantum dots and/or may be optically coupled to quantum dots. As is known in the art, a quantum dot is a semiconductor that may give off light based on the size of the quantum dot and the material from which it is made because of what is known as the quantum confinement effect. Thus, by coupling emitter optical resonator 202 having a particular peak wavelength(s) to a source of quantum dots of approximately the same peak wavelength(s), or constructing coupling emitter optical resonator 202 having a particular peak wavelength or wavelengths to include a source of quantum dots of approximately the same peak wavelength(s), emitter optical resonator 202 may function as a source of light which emits light at the peak wavelength or a plurality of peak wavelengths (e.g. a group of wavelengths or a continuous band of wavelengths).

In embodiments in which emitter optical resonator 202 includes quantum dots, quantum dots may be added to emitter optical resonator 202 using any suitable technique. For example, in embodiments where emitter optical resonator 202 comprises an optical ring, quantum dots may be formed within or adjacent to the optical ring using known semiconductor manufacturing techniques. As another example, in embodiments where emitter optical resonator 202 comprises an optical cavity, portions of the optical cavity may be coated with quantum dots created by colloidal synthesis.

Emitter optical resonator 202 may be coupled to functionalized optical resonator 206 via waveguide 204. Waveguide 204 may include any system, device, or apparatus to transmit light between emitter optical resonator 202 and functionalized optical resonator 206. In certain embodiments, waveguide 204 may comprise a dielectric waveguide, a structure in which a dielectric material with high permittivity, and thus high index of refraction (e.g., glass), is surrounded by a material with lower permittivity (e.g., air), permitting the waveguide to guide optical waves via total internal reflection.

As used herein, "agent" may refer to one or more atoms or molecules of any chemical, biological, and/or physical matter of which agent sensing system 200 may detect the presence. For example, an agent may include a hazardous substance such as a chemical or biological weapon, noxious gas, or other substance.

As discussed above, functionalized optical resonator 206 may have approximately the same peak wavelength(s) as emitter optical resonator 202. Functionalized optical resonator 206 may be "functionalized" to one or more specific agents to be detected by agent sensing system 200, such that the optical properties of functionalized optical resonator 206 are affected by the presence of the agent. For example, in embodiments where functionalized optical resonator 206 comprises an optical ring, an agent may be absorbed by functionalized optical resonator 206 which may alter its refractive index, which it turn may alter the peak wavelength (s) of functionalized optical resonator 206. As another example, in embodiments where functionalized optical resonator 206 comprises an optical cavity, an agent may absorb light within functionalized optical resonator 206, thus reducing the intensity of light present in the optical cavity. In some embodiments, functionalized optical resonator 206 may be formed by adding a thin film of material to an optical resonator to, wherein the thin film configured to attract or absorb an agent to be detected.

Functionalized optical resonator 206 may be coupled to reference optical resonator 210 via waveguide 208. Waveguide 208 may include any system, device, or apparatus to transmit light between functionalized optical resonator 206 and reference optical resonator 210. In certain embodiments, waveguide 208 may comprise a dielectric waveguide. In the same or alternative embodiments, waveguide 208 may be identical or similar to waveguide 204.

As discussed above, reference optical resonator 210 may have approximately the same peak wavelength(s) as emitter optical resonator 202 and functionalized optical resonator 206. Reference optical resonator 210 may be coupled to detection device 220 via waveguide 212. Waveguide 212 may include any system, device, or apparatus to transmit light between reference optical resonator 210 and detection device 220. In certain embodiments, waveguide 212 may comprise a dielectric waveguide. In the same or alternative embodiments, waveguide 212 may be identical or similar to waveguide 204 and/or waveguide 208.

Detection device 220 may include any system, device, or apparatus configured to detect light transmitted from reference optical resonator 210. In certain embodiments detection device may be identical or similar to detection device 120 of FIG. 1. In the same or alternative embodiments, detection device 220 may be optically coupled to reference optical resonator 210 via evanescent coupling, wherein detection device 220 may have a higher refractive index relative to reference optical resonator 210.

In operation, emitter optical resonator 202 may emit light at its peak wavelength(s) and waveguide 204 may transmit such light to functionalized optical resonator 206. If an agent to be detected is present, the agent may be absorbed by functionalized optical resonator 206, changing its peak wavelength(s). Such a shift may cause a mismatch between the peak wavelength(s) of functionalized optical resonator 206 and the wavelength(s) of light emitted by emitter optical resonator 202, such that functionalized optical resonator 206 filters the light emitted by emitter optical resonator 202. In the same or alternative embodiments, an agent present in or near functionalized optical resonator 206 may itself absorb the light emitted by emitter optical resonator 202, thus decreasing the intensity of light passing through functionalized optical resonator 206.

If the agent is not present, the peak wavelength(s) of functionalized optical resonator 206 may remain approximately matched to that of the wavelength(s) of light emitted by emitter optical resonator 202, such that the light emitted by emitter optical resonator 202 is not filtered, and may further transmit such light to reference optical resonator 210. Accordingly, the intensity of detected by detection device 220 may vary based on the presence or absence of the agent (e.g., light of the peak wavelength(s) of reference optical resonator 210 may be detected when the agent is not present, and little or no light of the peak wavelength(s) of reference optical resonator 210 may be detected when the agent is present).

FIG. 3 depicts a simplified schematic diagram illustrating another example agent sensing system 300, in accordance with embodiments of the present disclosure. As depicted in FIG. 3, agent sensing system 300 may include emitter optical resonator 302, functionalized optical resonator 306, reference optical resonator 310, waveguides 304, 308, and 312, and detection device 320. Notably, agent sensing system 300 is similar to agent sensing system 200 of FIG. 2, except that emitter optical resonator 302 of agent sensing system 300 is located between functionalized optical resonator 306 and reference optical resonator 310.

The operation of agent sensing system 300 may be similar to that of agent sensing system 200, except that any shift in peak wavelength(s) of functionalized optical resonator 306 will cause increased optical coupling of the light transmitted from optical resonator 302 to reference optical resonator 310. Thus, the intensity of detected by detection device 320 may vary based on the presence or absence of the agent (e.g., an increase of intensity of the peak wavelength(s) of reference optical resonator 310 may be detected when the agent is present).

FIG. 4 depicts a plan view of an example substrate 400 with selected components of the sensing system 200 of FIG. 2 formed thereon, in accordance with embodiments of the present disclosure. As shown in FIG. 4, each of emitter optical resonator 202, functionalized optical resonator 206, reference optical resonator 210, waveguides 204, 208, and 212, and detection device 220 may be formed as features on substrate 400. In certain embodiments, each of emitter optical resonator 202, functionalized optical resonator 206, reference optical resonator 210, and waveguides 204, 208, and 212 may be formed as separate features. In other embodiments, one or more of emitter optical resonator 202, functionalized optical resonator 206, reference optical resonator 210, and waveguides 204, 208, and 212 may be formed as a single feature.

Substrate 400 may include any suitable substrate, including without limitation silicon and/or other semiconductors. One or more of emitter optical resonator 202, functionalized optical resonator 206, reference optical resonator 210, and waveguides 204, 208, and 212 may be formed using any suitable fabrication technique, including photolithography. In these and other embodiments, emitter optical resonator 202, functionalized optical resonator 206, reference optical resonator 210, and waveguides 204, 208, and 212 may be made of chalcogenide glass formed on a silicon substrate.

FIG. 5 depicts a plan view of an example substrate 500 with selected components of agent sensing system 300 of FIG. 3 formed thereon, in accordance with embodiments of the present disclosure. As shown in FIG. 5, each of emitter optical resonator 302, functionalized optical resonator 306, reference optical resonator 310, waveguides 304, 308, and 312, and detection device 320 may be formed as features on substrate 500. In certain embodiments, each of emitter optical resonator 302, functionalized optical resonator 306, reference optical resonator 310, and waveguides 304, 308, and 312 may be formed as separate features. In other embodiments, one or more of emitter optical resonator 302, functionalized optical resonator 306, reference optical resonator 310, and waveguides 304, 308, and 312 may be formed as a single feature.

Substrate 500 may include any suitable substrate, including without limitation silicon and/or other semiconductors. One or more of emitter optical resonator 302, functionalized optical resonator 306, reference optical resonator 310, and waveguides 304, 308, and 312 may be formed using any suitable fabrication technique, including photolithography. In these and other embodiments, emitter optical resonator 302, functionalized optical resonator 306, reference optical resonator 310, and waveguides 304, 308, and 312 may be made of chalcogenide glass formed on a silicon substrate.

FIGS. 6A-6F depict a cross-sectional view of a substrate 600 during various stages of fabrication of selected components of an agent sensing system (e.g., agent sensing system 200 or agent sensing system 300), in accordance with embodiments of the present disclosure. Substrate 600 may include any suitable substrate, including without limitation silicon and/or other semiconductors. In certain embodiments, substrate 600 may be identical or similar to substrate 400 or substrate 500.

Figure 6B:
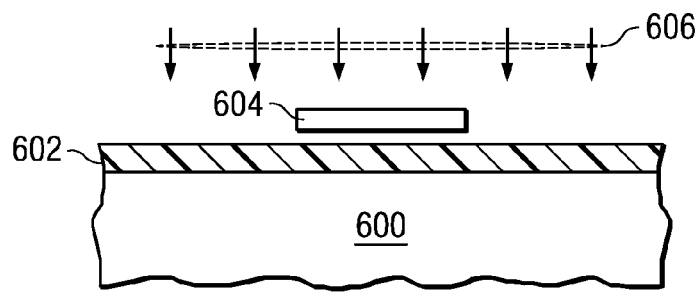
Figure 6C:
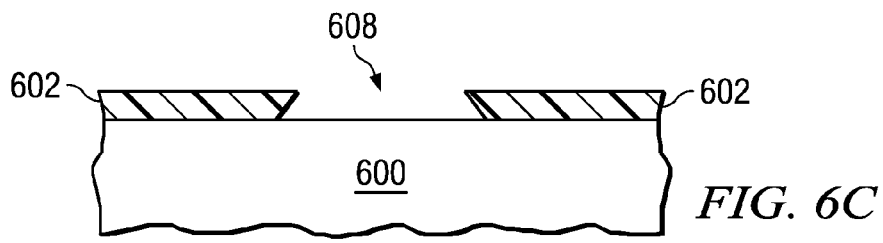

Referring to FIG. 6A, a substrate 600 may be coated with a photoresist layer 602. As shown in FIG. 6B, portions of photoresist layer 602 may be masked by a photomask 604 and exposed to ultraviolet light 606. As depicted in FIG. 6C, substrate 600 may be developed to remove portions of photoresist layer 602 masked by photomask 604.

Figure 6D:
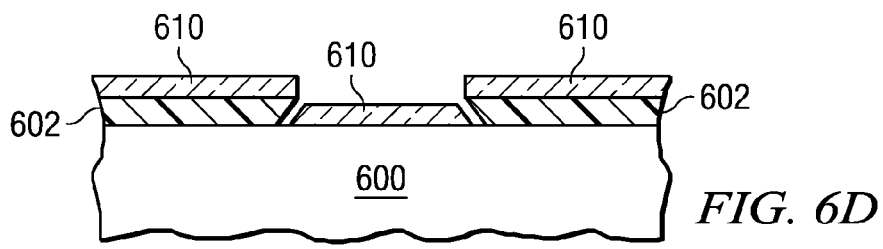

As shown in FIG. 6D, a glass 610 may be deposited upon substrate 600 and remaining portions of photoresist layer 602. In certain embodiments, glass 610 may comprise a chalcogenide glass (e.g., $Ge_{23}SB_7S_{70}$). To deposit glass 610, bulk glass may be prepared using traditional chalcogenide melt-quenching techniques. The glass 610 may then be deposited onto substrate using thermal evaporation or any other suitable deposition technique.

Figure 6E:
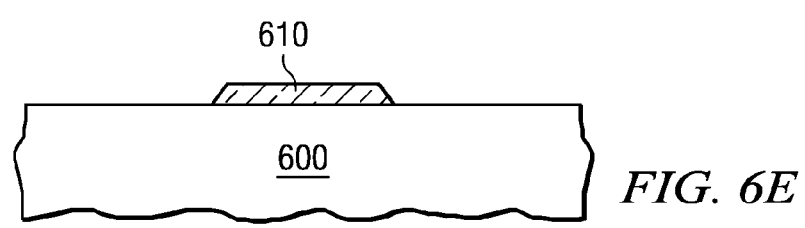

As depicted in FIG. 6E, the remaining portions of photoresist layer 602 may be removed (e.g., by sonicating in a solvent such as acetone to dissolve photoresist layer 602), thus lifting off the portions of glass 610 deposited onto the remaining portions of photoresist layer 602. The remaining glass 610 may form one or more structures that form waveguides (e.g., waveguides 204, 208, 212, 304, 308, and/or 312) and/or optical rings (e.g., emitter optical resonators 202, 302, functionalized optical resonators 206, 306, and/or reference optical resonators 210, 310).

Figure 6F:
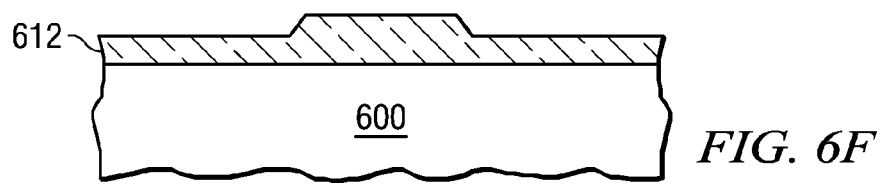

In certain embodiments, the additional fabrication step depicted in FIG. 6F may be undertaken. As shown in FIG. 6F, additional glass may be deposited upon substrate 600. The additional glass may form a structure 612 that may form a rib waveguide and/or rib optical ring, as opposed to the glass structure of FIG. 6E which may form a strip waveguide and/or strip optical ring.

Advantages of the methods and systems described herein may include an agent sensing system that may be formed on the same integrated circuit as a photodetector (e.g., a focal plane array), thus permitting a system of smaller physical size as compared with traditional approaches. Accordingly, power consumption, cost, weight and size may be reduced as compared with traditional approaches. The systems and methods disclosed herein may also permit combination of a agent sensing system and optical sensing system into one device.

In addition, because the methods and systems detect a shift in peak wavelength(s) of an optical element caused by the presence of an agent, as compared to detecting absorption by the agent itself, the systems and methods herein may provide greater accuracy over that of traditional approaches.

Although the embodiments in the disclosure have been described in detail, numerous changes, substitutions, variations, alterations, and modifications may be ascertained by those skilled in the art. Additionally or alternatively, while the disclosure may be described predominantly in reference to infrared detectors, the embodiments disclosed herein may be utilized with many types of detectors including, but not limited to, visible, infrared, ultraviolet, x-ray, or other radiation detectors. It is intended that the present disclosure encompass all such changes, substitutions, variations, alterations and modifications as falling within the spirit and scope of the appended claims.

What is claimed is:

1. An agent sensing system, comprising:
    an emitter optical resonator configured to emit light at one or more system peak wavelengths;
    a functionalized optical resonator optically coupled to the emitter optical resonator and configured to:
    receive the emitted light at a first intensity from the emitter optical resonator;
    propagate the emitted light in the absence of a particular agent; and
    filter the emitted light in the presence of the particular agent; and
    a non-functionalized reference optical resonator optically coupled to the functionalized optical resonator and configured to receive and propagate light from the functionalized optical resonator such that a second intensity of the light propagated by the non-functionalized reference optical resonator is based at least on whether the light emitted by the emitter optical resonator is filtered or propagated by the functionalized optical resonator; and
    a photosensitive device coupled to at least the non-functionalized reference optical resonator and configured to detect the second intensity of light propagating in the non-functionalized reference optical resonator, and to sense the particular agent based on a change between the first and second intensities.

2. The agent sensing system of claim 1, wherein the second intensity of light propagated by the non-functionalized reference optical resonator is greater in the absence of the particular agent relative to the second intensity of light propagated by the non-functionalized reference optical resonator in the presence of the particular agent.

3. The agent sensing system of claim 1, wherein the non-functionalized reference optical resonator is further optically coupled and the second intensity of light propagated by the non-functionalized reference optical resonator is greater in the presence of the particular agent relative to the second intensity of light propagated by the non-functionalized reference optical resonator in the absence of the particular agent.

4. The agent sensing system of claim 1, wherein the material of the functionalized optical resonator has first refractive index in the absence of the particular agent and a second refractive index in the presence of the particular agent.

5. The agent sensing system of claim 1, wherein the functionalized optical resonator has one or more first peak wavelengths approximately equal to the one or more system peak wavelengths in the absence of the particular agent and one or more second peak wavelengths substantially not equal to the one or more system peak wavelengths in the presence of the particular agent.

6. The agent sensing system of claim 1, wherein the non-functionalized reference optical resonator has one or more peak wavelengths approximately equal to the one or more system peak wavelengths.

7. The agent sensing system of claim 1, further comprising a waveguide optically coupling the emitter optical resonator to the functionalized optical resonator.

8. The agent sensing system of claim 3, further comprising a waveguide optically coupling the emitter optical resonator to the non-functionalized reference optical resonator.

9. The agent sensing system of claim 1, further comprising a waveguide optically coupling the functionalized optical resonator to the non-functionalized reference optical resonator.

10. The agent sensing system of claim 1, wherein the photosensitive device is an integral part of a focal plane array.

11. The agent sensing system of claim 1, further comprising a processing unit communicatively coupled to the photosensitive device.

12. The agent sensing system of claim 1, wherein the emitter optical resonator, functionalized optical resonator, and non-functionalized reference optical resonator are all formed on a substrate.

13. The agent sensing system of claim 1, wherein at least one of the emitter optical resonator, functionalized optical resonator, and non-functionalized optical resonator comprises chalcogenide glass.

14. The agent sensing system of claim 1, wherein at least one of the emitter optical resonator, functionalized optical resonator, and non-functionalized optical resonator comprises an optical ring.

15. The agent sensing system of claim 1, wherein the emitter optical resonator comprises a plurality of quantum dots configured to emit light approximately at the one or more system peak wavelengths.

16. A method of manufacture comprising:
    forming, by way of photolithography, an emitter optical ring on a substrate, the emitter optical ring configured to emit light, of a first intensity, at one or more system peak wavelengths;
    forming, by way of photolithography, a functionalized optical resonator optically coupled to the emitter optical resonator on the substrate, the functionalized optical resonator configured to:
    propagate light emitted by the emitter optical ring in the absence of a particular agent; and
    filter light emitted by the emitter optical ring in the presence of the particular agent; and
    forming, by way of photolithography, a non-functionalized reference optical resonator optically coupled to the functionalized and configured to receive and propagate light from the functionalized optical resonator such a second intensity of the light propagated by the non-functionalized reference optical resonator is based at least on whether light emitted by the emitter optical resonator is filtered or propagated by the functionalized optical resonator; and
    forming a photosensitive device coupled to the non-functionalized reference optical resonator and configured to detect the second intensity of light propagating in the reference optical resonator, and sense the particular agent based on a change between the first and second intensities.

17. The method of claim 16, wherein at least one of forming the emitter optical resonator, forming the functionalized optical resonator, and forming the non-functionalized optical resonator comprises a depositing a chalcogenide glass on the substrate.

18. A method for sensing an agent, comprising:
- emitting light, of a first intensity, at one more system peak wavelengths;
- optically coupling a functionalized optical resonator to the emitted light;
- propagating the emitted light via the functionalized optical resonator in the absence of a particular agent;
- filtering the emitted light by the functionalized optical resonator in the presence of the particular agent;
- optically coupling a non-functionalized reference optical resonator to the functionalized optical resonator to propagate light emitted from the functionalized optical resonator via the non-functionalized reference optical resonator; and
- detecting a second intensity of the light propagated by the non-functionalized reference optical resonator; and
- sensing the particular agent based on a change between the first and second intensities.

* * * * *

UNITED STATES PATENT AND TRADEMARK OFFICE
CERTIFICATE OF CORRECTION

PATENT NO. : 8,394,329 B2  Page 1 of 1
APPLICATION NO. : 12/503264
DATED : March 12, 2013
INVENTOR(S) : Frank B. Jaworski et al.

It is certified that error appears in the above-identified patent and that said Letters Patent is hereby corrected as shown below:

On the title page of the patent,
"(75) Inventors: Frank B. Jaworski, Goleta, CA (US)
Anuradha M. Agarwal, Weston, MA (US)"

Should be replaced with
--(75) Inventors: Frank B. Jaworski, Goleta, CA (US)
Anuradha M. Agarwal, Weston, MA (US)
Juejun Hu, Newark, DE (CN)--

Signed and Sealed this
Eighth Day of March, 2016

Michelle K. Lee
*Director of the United States Patent and Trademark Office*